United States Patent
Kumagai et al.

(10) Patent No.: US 10,345,232 B2
(45) Date of Patent: Jul. 9, 2019

(54) METHOD OF MEASURING STATE OF CONCRETE

(71) Applicant: TOPCON CORPORATION, Tokyo (JP)

(72) Inventors: Kaoru Kumagai, Tokyo (JP); Shugo Akiyama, Tokyo (JP); Issei Hanya, Tokyo (JP); Peng Zhao, Tokyo (JP); Masashi Funahashi, Tokyo (JP); Yoshimitsu Nakajima, Tokyo (JP); Yuji Shirane, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 0 days.

(21) Appl. No.: 16/065,971

(22) PCT Filed: Dec. 21, 2016

(86) PCT No.: PCT/JP2016/088055
§ 371 (c)(1),
(2) Date: Jun. 25, 2018

(87) PCT Pub. No.: WO2017/110853
PCT Pub. Date: Jun. 29, 2017

(65) Prior Publication Data
US 2019/0017929 A1 Jan. 17, 2019

(30) Foreign Application Priority Data
Dec. 25, 2015 (JP) .................................. 2015-254407

(51) Int. Cl.
*G01N 21/35* (2014.01)
*G01N 33/38* (2006.01)
(Continued)

(52) U.S. Cl.
CPC ......... *G01N 21/359* (2013.01); *G01N 33/383* (2013.01); *G01N 21/274* (2013.01)

(58) Field of Classification Search
CPC ... G01N 21/274; G01N 21/359; G01N 33/383
See application file for complete search history.

(56) References Cited

U.S. PATENT DOCUMENTS

2007/0218174 A1 9/2007 Hanamatsu et al.

FOREIGN PATENT DOCUMENTS

| CA | 2 559 590 | 9/2005 |
| CN | 1930465 | 3/2007 |

(Continued)

OTHER PUBLICATIONS

International Search Report dated Mar. 21, 2017 in International (PCT) Application No. PCT/JP2016/088055.

*Primary Examiner* — Mark R Gaworecki
(74) *Attorney, Agent, or Firm* — Wenderoth, Lind & Ponack, L.L.P.

(57) ABSTRACT

A method of measuring a state of concrete includes emitting an irradiation light to the concrete, the irradiation light including a wavelength range of near infrared light related to concrete measurement; and receiving a reflection light of the irradiation light P reflected on the concrete. At least five wavelengths λ1 to λ5, λ6 to λ10, different from each other by PLS regression analysis within a wavelength range of 900 nm to 2500 nm of absorption spectrum, are determined, and a degree of neutralization of the concrete caused by calcium hydroxide and a concentration of chloride ion is estimated.

3 Claims, 3 Drawing Sheets

(51) Int. Cl.
*G01N 21/27* (2006.01)
*G01N 21/359* (2014.01)

(56) References Cited

FOREIGN PATENT DOCUMENTS

| | | |
|---|---|---|
| EP | 1 724 566 | 11/2006 |
| JP | 5-273125 | 10/1993 |
| JP | 2008-122412 | 5/2008 |
| JP | 2011-214940 | 10/2011 |
| JP | 5031281 | 7/2012 |
| KR | 10-2006-0122941 | 11/2006 |
| TW | 200532174 | 10/2005 |
| WO | 2005/088273 | 9/2005 |
| WO | 2010/046968 | 4/2010 |

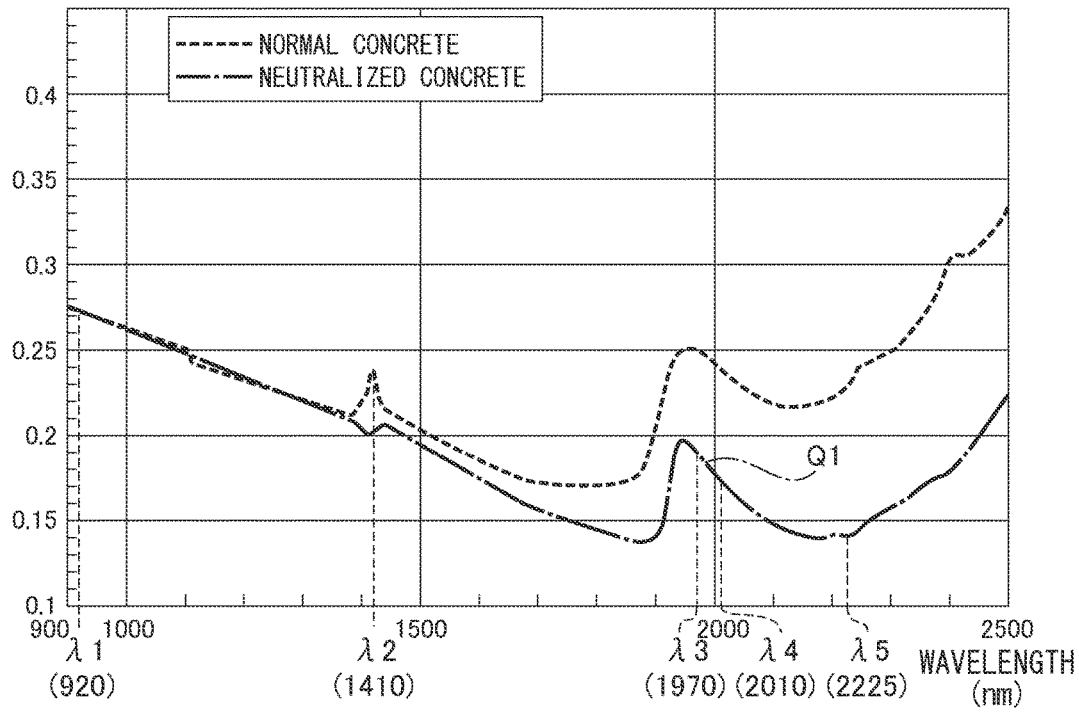
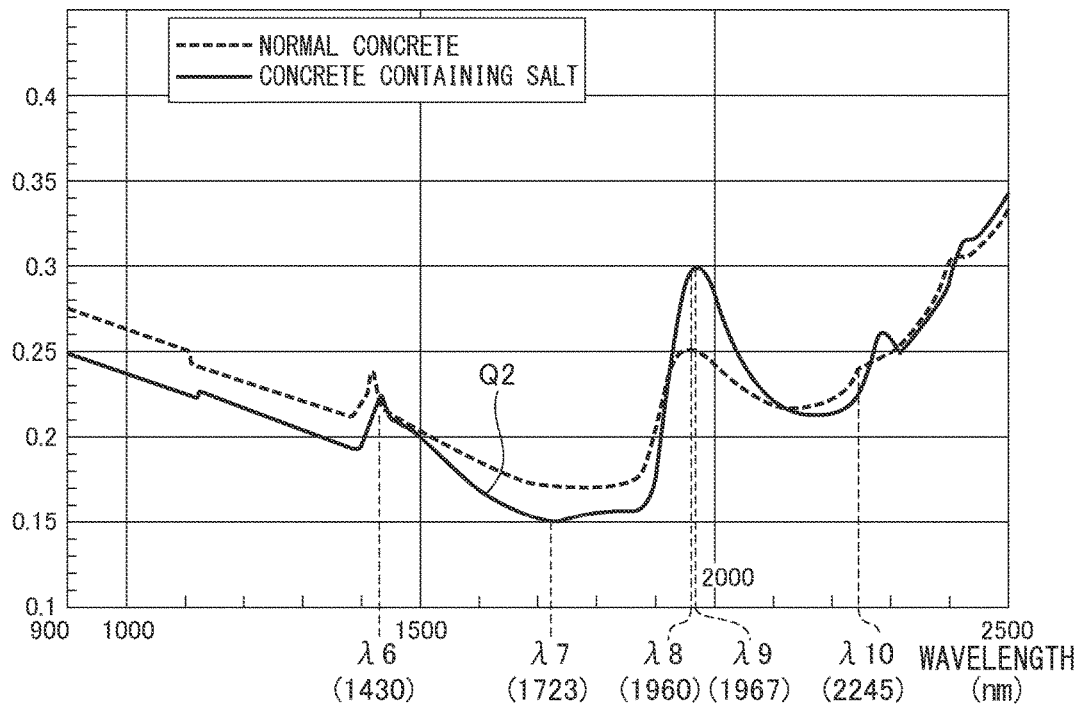

METHOD OF MEASURING STATE OF CONCRETE

CROSS-REFERENCE TO RELATED APPLICATION

The present application is based on and claims priority to Japanese Patent Application No. 2015-254407, filed on Dec. 25, 2015, the disclosure of which is hereby incorporated by reference in its entirety.

TECHNICAL FIELD

This disclosure relates to a method of measuring a state of concrete. The method is capable of optically detecting chloride content contained in the concrete and a degree of neutralization thereof.

BACKGROUND ART

Conventionally, a method of measuring a state of concrete which can optically detect chloride content contained in the concrete and a degree of neutralization thereof has been taught by, for example, JP 5031281 B (Patent Literature 1). The method of Patent Literature 1 detects deterioration of concrete based on absorption spectrum in a predetermined wavelength range of near infrared light reflected by a concrete building.

The method of Patent Literature 1 uses a wavelength range of 900 nm to 1700 nm of the absorption spectrum to detect concentration of calcium hydroxide so as to determine or measure the neutralization of the concrete, as the neutralization has correlation with the deterioration of the concrete. The method also uses a wavelength range of 1700 nm to 2500 nm of the absorption spectrum to detect concentration of chloride ion so as to determine or measure the salt damage, as the salt damage has correlation with the deterioration of the concrete.

According to the technique taught by Patent Literature 1, it is possible to accurately determine or measure the deterioration of concrete using a nondestructive method.

Technical Problem

The method disclosed by Patent Literature 1 executes spectroscopic analysis on a predetermined wavelength range of absorption spectrum using a spectroscopy to detect concentration of calcium hydroxide and ion concentration of a chloride. Thus, it is possible to accurately detect concentration of calcium hydroxide and/or ion concentration of a chloride, but it makes the measuring device complex and increases the manufacturing cost of the measuring device, disadvantageously.

This disclosure has been developed in view of the above problem. That is, an object of the disclosure is to provide a method of measuring concrete capable of easily determining or measuring deterioration of the concrete without using a spectroscopy while maintaining the estimation accuracy.

SUMMARY OF THE INVENTION

A method of measuring a state of concrete of this disclosure emits an irradiation light to the concrete, the irradiation light including a wavelength range of near infrared light related to concrete measurement; receives a reflection light of the irradiation light reflected on the concrete; determines at least five wavelengths different from each other by PLS regression analysis within a wavelength of 900 nm to 2500 nm of absorption spectrum; and estimates a degree of neutralization of the concrete caused by calcium hydroxide and a concentration of chloride ion.

BRIEF DESCRIPTION OF DRAWINGS

FIG. 2 is a graph of characteristic curves showing changes of absorption spectrum in response to deterioration of the concrete, particularly a graph showing spectral distribution curves for different concentrations of calcium hydroxide. FIG. 3 is a graph of characteristic curves showing changes of absorption spectrum in response to deterioration of the concrete, particularly a graph showing spectral distribution curves for different concentrations of chloride ion.

DETAILED DESCRIPTION OF THE PREFERRED EMBODIMENTS

Embodiment

A method of measuring a state of concrete according to the present disclosure will be described hereinafter with reference to drawings.

FIG. 1 to FIG. 4 are explanatory views for the method of measuring concrete according to an embodiment of the present invention.

Figure 1:
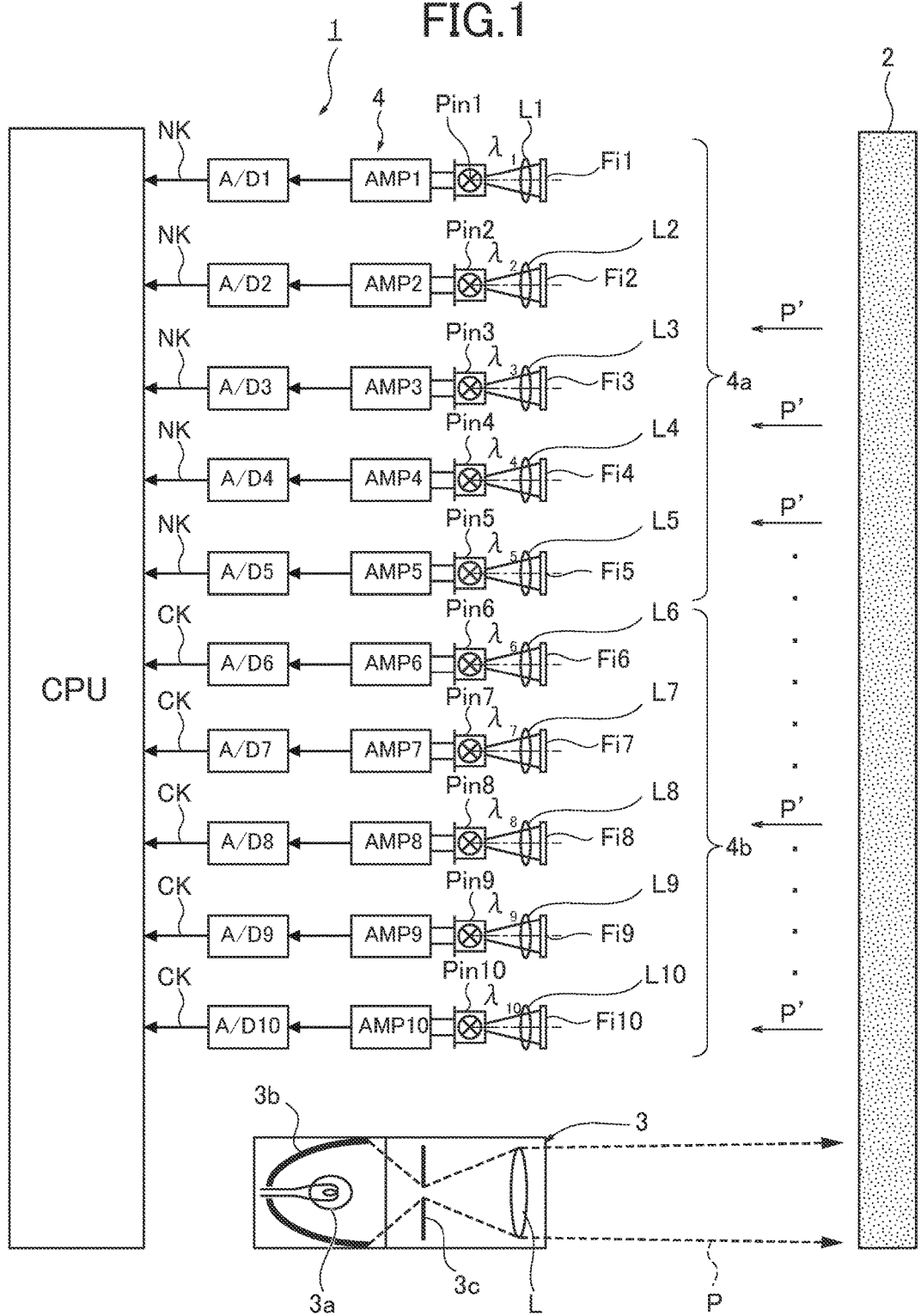
FIG. 1 is a block diagram illustrating a schematic configuration of a measuring device which is used for a method of measuring a state of concrete according to the disclosure.

FIG. 1 is an optical block diagram of a measuring device which is used for the method of measuring a state of concrete according to an embodiment of the disclosure.

In FIG. 1, the concrete measuring device is annotated by a reference sign 1, and concrete is annotated by a reference number 2. The measuring device 1 includes at least a computer CPU, a light source 3, and a light receiving part 4.

The light source 3 emits an irradiation light P having a wavelength range of near infrared light (e.g., a wavelength range of 780 nm to 2500 nm) to the concrete 2 in order to measure a state of the concrete 2. The light source 3 includes, for example, a halogen lamp 3a, a reflection mirror 3b, an aperture member 3c, and a condenser lens L to collect the irradiation light P to emit the collected light as a parallel light flux.

The irradiation light P is reflected by the concrete 2, and the reflected light P' is received by the light receiving part 4. The light receiving part 4 receives the reflected lights P' of at least five different wavelengths within a wavelength range of 900 nm to 2500 nm of an absorption spectrum.

The above-mentioned five different wavelengths or more are used to estimate a degree of neutralization caused by calcium hydroxide, which has an influence to the neutralization, and to estimate concentration of chloride ion, which has an influence to salt damage. Here, the degree of neutralization may be determined by estimating the concentration of the calcium hydroxide or by estimating a pH value thereof.

The at least five different wavelengths are determined by PLS regression analysis. FIG. 2 is an explanatory view showing a spectral distribution curve acquired from normal concrete 2 and a spectral distribution curve acquired from neutralized concrete 2.

In FIG. 2, the broken line represents the spectral distribution curve acquired from the normal concrete 2, and the dash-dotted line represents the spectral distribution curve acquired from the neutralized concrete 2.

The spectral distribution curve Q1 acquired from the neutralized concrete 2 varies in response to the degree of neutralization (e.g., concentration of calcium hydroxide or pH). Wavelengths λ1 to λ5 are determined or selected using the PLS regression analysis by acquiring multiple spectral distribution curves Q1.

Similarly, the spectral distribution curve Q2 acquired from the concrete 2 containing salt varies in response to the salinity concentration thereof, as shown in FIG. 3. Wavelengths λ6 to λ10 are determined or selected using the PLS regression analysis by acquiring multiple spectral distribution curves Q2.

Figure 4:
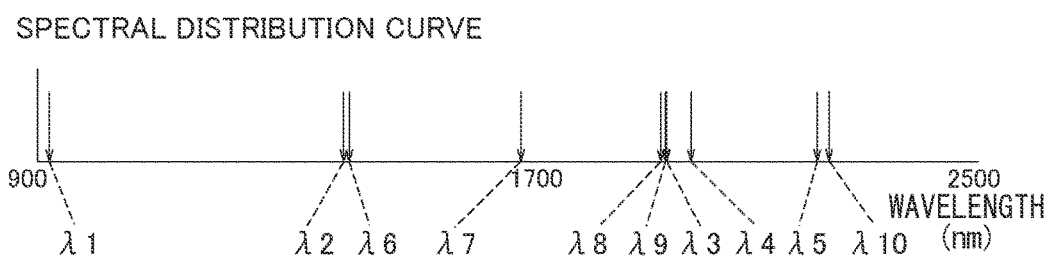
FIG. 4 is an explanatory view showing wavelengths determined by partial least squares regression analysis (PLS regression analysis).

As shown in FIG. 4, the degree of neutralization caused by calcium hydroxide is estimated in accordance with the two wavelengths λ1, λ2 within the wavelength range of 900 nm to 1700 nm of the absorption spectrum as well as with the three wavelengths λ3 to λ5 within the wavelength range of 1700 nm to 2500 nm of the absorption spectrum. The concentration of chloride ion is estimated in accordance with the wavelength λ6 within the wavelength range of 900 nm to 1700 nm of the absorption spectrum as well as with the four wavelengths λ7 to λ10 within the wavelength range of 1700 nm to 2500 nm of the absorption spectrum.

On the basis of a true value of the degree of neutralization of the concrete 2, a true value of the concentration of chloride ion, as well as the determined wavelengths λ1 to λ5 and λ6 to λ10; a calibration curve related to the degree of neutralization and a calibration curve related to the concentration of the chloride ion are drawn through multiple regression analysis. An estimation coefficient related to the degree of neutralization and an estimation coefficient related to the concentration of chloride ion are then determined. Here, the true value of the degree of neutralization represents an ion concentration value of the calcium hydroxide obtained from a method used in a known quantitative analysis or a pH value thereof. The true value of the concentration of chloride ion represents a concentration value of the chloride ion. In FIG. 2 to FIG. 4, the horizontal line represents wavelengths and the vertical line represents reflectance or transmittance.

The light receiving part 4 includes light receiving sections 4a and 4b. For example, the light receiving section 4a is to estimate the degree of neutralization of the concrete 2 caused by calcium hydroxide, and the light receiving section 4b is to estimate the concentration of the chloride ion contained in the concrete 2.

The light receiving section 4a includes filters Fi1 to Fi5. The filters Fi1 to Fi5 allow the reflection lights P' having the wavelengths λ1 (λ1=920 nm), λ2 (λ2=1410 nm), λ3 (λ3=1970 nm), λ4 (λ4=2010 nm), and λ5 (λ5=2225 nm), and thereabout to pass through, respectively.

The reflection lights P' passed through the corresponding filters Fi1 to Fi5 are collected by the corresponding condenser lenses L1 to L5, respectively. The collected lights are then photoelectrically converted by corresponding Pin-photodiodes Pin 1 to Pin 5, amplified by corresponding amplifiers AMP1 to AMP5, digitally converted by analog-digital converters A/D1 to A/D5, and inputted to the CPU as signals NK to detect the degree of neutralization of the concrete 2, respectively.

The light receiving part 4b includes filters Fi6 to Fi10. The filters Fi6 to Fi10 allow the reflection lights P' having the wavelengths λ6 (λ6=1430 nm), λ7 (λ7=1723 nm), λ8 (λ8=1960 nm), λ9 (λ9=1967 nm), and λ10 (λ10=2245 nm), and thereabout to pass through, respectively.

The reflection lights P' passed through the corresponding filters Fi6 to Fi10 are collected by the corresponding condenser lenses L6 to L10, respectively. The collected lights are then photoelectrically converted by corresponding Pin-photodiodes Pin 6 to Pin 10, amplified by corresponding amplifiers AMP6 to AMP10, digitally converted by analog-digital converters A/D6 to A/D10, and inputted to the CPU as signals CK to detect the concentration of the chloride ion of the concrete 2, respectively.

The CPU stores the estimation coefficient to estimate the degree of neutralization of the concrete 2 and the estimation coefficient to estimate the concentration of chloride ion thereof. The CPU estimates the degree of neutralization and the concentration of chloride ion in accordance with the signals NK, CK, and the estimation coefficients.

In this embodiment, the degree of neutralization caused by calcium hydroxide and the concentration of chloride ion are estimated based on the lights within the wavelength range of 900 nm to 2500 nm, which are used to measure the deterioration of the concrete, without classifying the wavelength ranges of the absorption spectrum. As a result, it is possible to measure the deterioration of the concrete 2 without using a spectroscopy to spectrally disperse the absorption spectrum while maintaining the accuracy.

The invention claimed is:

1. A method of measuring a state of concrete, the method comprising:
    emitting an irradiation light to concrete, the irradiation light including a wavelength range of near infrared light;
    receiving a reflection light of the irradiation light reflected on the concrete;
    determining at least five wavelengths different from each other by PLS regression analysis within a wavelength range of 900 nm to 2500 nm of absorption spectrum; and
    estimating a degree of neutralization of the concrete caused by calcium hydroxide and a concentration of chloride ion,
    wherein the degree of neutralization caused by the calcium hydroxide is estimated based on a pH value.

2. The method according to claim 1, wherein the degree of neutralization caused by the calcium hydroxide is estimated using two wavelengths within the wavelength range of 900 nm to 2500 nm of the absorption spectrum and three wavelengths within the wavelength range of 1700 nm to 2500 nm, and
    the concentration of the chloride ion is estimated using one wavelength within the wavelength range of 900 nm to 1700 nm of the absorption spectrum and four wavelengths within the wavelength range of 1700 nm to 2500 nm.

3. The method according to claim 1, wherein the wavelengths used to estimate the degree of neutralization caused by the calcium hydroxide are about 920 nm, 1410 nm, 1970 nm, 2010 nm, and 2225 nm; and
    the wavelengths used to estimate the concentration of chloride ion are about 1430 nm, 1723 nm, 1960 nm, 1967 nm, and 2245 nm.

* * * * *